(12) United States Patent
Zamora et al.

(10) Patent No.: US 6,765,069 B2
(45) Date of Patent: Jul. 20, 2004

(54) PLASMA CROSS-LINKED HYDROPHILIC COATING

(75) Inventors: Paul O. Zamora, Gaithersburg, MD (US); Meng Chen, Silver Springs, MD (US); Shigemas Osaki, Sandy, UT (US); Ting-Ting Hsieh, Midvale, UT (US); Ray Tsang, Salt Lake City, UT (US)

(73) Assignee: BioSurface Engineering Technologies, Inc., College Park, MD (US)

( * ) Notice: Subject to any disclaimer, the term of this patent is extended or adjusted under 35 U.S.C. 154(b) by 96 days.

(21) Appl. No.: 10/260,510

(22) Filed: Sep. 27, 2002

(65) Prior Publication Data

US 2003/0091827 A1 May 15, 2003

Related U.S. Application Data

(60) Provisional application No. 60/326,048, filed on Sep. 28, 2001.

(51) Int. Cl.[7] .................. C08G 65/331; C08G 65/332; C08G 65/333; A61M 25/00
(52) U.S. Cl. ................ 525/404; 525/54.3; 525/59; 525/61; 525/294; 525/296; 525/301; 525/302; 525/205; 525/309; 525/326.9; 525/329.4; 525/329.9; 525/330.5; 525/405; 525/407; 525/408; 525/409; 528/110; 528/405; 528/421; 536/123.1; 604/93.01
(58) Field of Search .......................... 525/54.3, 59, 61, 525/294, 296, 301, 302, 303, 305, 309, 326.9, 329.4, 329.9, 330.5, 404, 405, 407, 408, 409; 528/110, 405, 421; 536/123.1; 604/93.01

(56) References Cited

U.S. PATENT DOCUMENTS

| | | | |
|---|---|---|---|
| 4,844,986 A | 7/1989 | Karakelle et al. ............ 428/447 |
| 5,132,108 A | 7/1992 | Narayanan et al. ....... 424/78.17 |
| 5,153,072 A | 10/1992 | Ratner et al. ................ 428/461 |
| 5,244,654 A | 9/1993 | Narayanan et al. ....... 424/78.17 |
| 5,338,770 A | 8/1994 | Winters et al. ............. 523/112 |
| 5,455,040 A | 10/1995 | Marchant .................... 424/426 |
| 5,463,010 A | 10/1995 | Hu et al. ....................... 528/25 |
| 5,486,357 A | 1/1996 | Narayanan ............... 424/78.17 |
| 5,507,804 A * | 4/1996 | Llanos ...................... 623/6.11 |
| 5,509,899 A | 4/1996 | Fan et al. ...................... 604/96 |
| 5,650,234 A | 7/1997 | Dolence et al. ............. 428/447 |
| 6,049,736 A | 4/2000 | Stewart et al. ............. 607/116 |
| 6,169,127 B1 | 1/2001 | Lohmann et al. ........... 523/106 |
| 6,248,057 B1 * | 6/2001 | Mavity et al. ................. 600/3 |
| 6,265,016 B1 | 7/2001 | Hostettler et al. ......... 427/2.11 |
| 6,348,558 B1 | 2/2002 | Harris et al. ................ 528/196 |
| 6,372,283 B1 | 4/2002 | Shim et al. ................ 427/2.25 |
| 6,376,604 B2 | 4/2002 | Kozlowski ................. 525/54.2 |
| 6,440,571 B1 | 8/2002 | Valient, Jr. et al. ......... 428/447 |
| 6,444,324 B1 | 9/2002 | Yang et al. ................. 428/447 |
| 2002/0049281 A1 | 4/2002 | Zhao et al. ................. 525/54.3 |

FOREIGN PATENT DOCUMENTS

| | | | | |
|---|---|---|---|---|
| JP | 08257112 A | * | 10/1996 | ........... A61L/29/00 |
| WO | WO01/45862 A1 | | 6/2001 | |
| WO | WO02/053664 A2 | | 7/2003 | |

* cited by examiner

*Primary Examiner*—Robert Sellers
(74) *Attorney, Agent, or Firm*—Stephen A. Slusher; Peacock, Myers & Adams, P.C.

(57) ABSTRACT

A method for making a hydrophilic and lubricious coating, the coating so made and a medical device including such coating, wherein the coating includes a hydrophilic polymeric unit layer cross-linked with a plasma deposited double bond monomer. The hydrophilic polymeric unit can include ethylene oxide with one or more primary or secondary alcohol groups or glycosaminoglycans such as hyaluronic acid, and the double bond monomer includes monomers containing at least one double bond, preferably a C=C, C=N or C=O bond, including N-trimethylsilyl-allylamine, ethylene, propylene and allyl alcohol. The invention also provides products containing such coatings and their uses in medical, pharmaceutical and cosmetic applications.

7 Claims, 3 Drawing Sheets

PLASMA CROSS-LINKED HYDROPHILIC COATING

CROSS-REFERENCE TO RELATED APPLICATION

This application claims the benefit of U.S. Provisional Patent Application Serial No. 60/326,048, entitled "Plasma Cross-Linked Hydrophilic Coating", filed on Sep. 28, 2001, and the specification thereof is incorporated herein by reference.

BACKGROUND OF THE INVENTION

1. Field of the Invention (Technical Field)

The present invention relates to materials, methods and processes for making a hydrophilic and lubricious coating, wherein a hydrophilic polymeric unit is cross-linked by means of a plasma process with a double bond monomer, wherein the coating optionally further includes a bifunctional spacer to which the hydrophilic polymeric unit is bound. Also provided is the hydrophilic and lubricious coating and medical devices including the coating.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

For many medical devices, it is preferable if a coating or other contacting surface has several properties, including biocompatibility and lubricity. Device surfaces and coatings that are water absorbent and lubricious may be effectively employed with, for example, stents, screws, tubing, catheters, wire guides, needles, sutures, and the like. Coatings that are hydrophilic and lubricious can be contacted with tissues with decreased trauma. For example, any medical device, such as a bandage, suture, tubing, catheter, guide wire and the like, may be more conveniently removed with less trauma to associated tissue if the surface is lubricious.

Similarly, it is a requirement for medical device surfaces that the surface or other coating be biocompatible. Any implantable medical device requires biocompatibility, in order to avoid adverse reactions. In normal application, such devices are expected to function in intimate contact with living tissue and blood. This contact requires a delicate balance between ensuring that the device can function in the complex extra- and intra-cellular environment and maintaining the living tissues and blood.

Lubricity is, in part, related to biocompatibility and thromboresistance, particularly since the degree of lubricity of a coating is related to wear of the coating due to contact with other surfaces. For devices, such as needles, sutures, catheters and the like, that transit tissue or abrasive substrates, a high degree of lubricity is desired, concomitant with biocompatibility and a high degree of wear resistance. Thus coatings that are lubricious, but are not resistant to contact with tissue or abrasive substrates, do not function well in medical devices.

Long-term use of most polymeric substrates frequently results in mechanical failure, the promotion of blood clot formation, or physical degradation due to unfavorable interactions with tissue or blood environments. Thus it is desirable to have coatings or other composites for polymeric substrates that are hydrophilic and lubricious, provide superior strength, do not promote blood clot formation, and which do not interact with the tissue or blood environment. The specific requirements of each device vary depending on the degree and duration of contact and the nature of the application.

Cross-linking of polymers to form a lubricious surface has been explored. For example, International Patent Application WO 02/053664, entitled *Absorbent, Lubricious Coating and Articles Coated Therewith*, discloses a coating consisting of a cross-linked hydrogel copolymer including water soluble base polymers with graft polymerized organic moieties that react with water to form a silanol group, wherein the copolymer is cross-linked through the silanol groups. However, in this coating and method the crosslinking is solely through the silane groups, forming an Si—O—Si cross-link. U.S. patent Application No. 2002/0049281, *Process for Cross-Linking Hyaluronic Acid to Polymers*, discloses a method for double crosslinking of hyaluronic acid derivatives, presumably with one bond formed by cross-linking via hydroxyl groups and the other via, for example, carboxyl groups. However, this method requires lengthy reactions, up to forty-eight hours, and extreme pH changes, ranging from less than pH 4 to pH 12. U.S. Pat. No. 6,169,127, entitled Plasma-Induced Polymer Coatings, discloses coatings for contact lenses utilizing after-glow plasma-induced polymerization of an unsaturated monomeric compound, with cross-linking by concurrent after-glow plasma-induced polymerization of two monomers, such as a primary monomeric vinyl compound and a cross-linking agent. This method requires co-polymerization of the two monomers, and does not permit prior application of a monomer or polymeric unit to be subsequently cross-linked or chemical complexation of a monomer or polymeric unit to a linking moiety with the crosslinking subsequent to such complexation.

Prior art coatings employing plasma polymerization are known in the art. These include the coatings and methods disclosed in U.S. Pat. No. 5,463,010, to Hu, et al., entitled *Hydrocyclosiloxane Membrane Prepared By Plasma Polymerization Process*; and U.S. Pat. No. 5,650,234, to Dolence et al., entitled *Electrophilic Polyethylene Oxides for the Modification of Polysaccharides, Polypeptides (Proteins) and Surfaces*. However, these methods do not disclose plasma crosslinking utilizing a polymerizable hydrophilic polymeric unit in conjunction with a plasma consisting of a double bond monomer.

None of the preceding references disclose coatings or methods wherein base hydrophilic polymeric units applied by conventional means, such as dipping, are subsequently cross-linked by plasma polymerization of a monomer, such as a double bond monomer, resulting in a hydrophilic and lubricious coating.

SUMMARY OF THE INVENTION (DISCLOSURE OF THE INVENTION)

In one embodiment the invention provides a plasma cross-linked hydrophilic and lubricious coating wherein a hydrophilic polymeric unit is cross-linked in situ with a plasma deposited double bond monomer. The hydrophilic polymeric unit can be an ethylene oxide with one or more primary or secondary alcohol groups, including in a preferred embodiment 2,2'[(methylethylidine)-bis(4,1-phenyleneoxymethylene)]-bis-oxirane-polymer (PEOC). Alternatively, the hydrophilic polymeric unit can be a glycosaminoglycan, including a long chain linear polysaccharide such as hyaluronic acid, hyaluronan, dextran, cellulose or methyl cellulose. Preferably the double bond monomer includes a C=C, C=N or C=O double bond, and in a preferred embodiment is N-trimethylsilyl-allylamine (TMSAA), ethylene, propylene or allyl alcohol. The coating can also include a bifunctional spacer covalently bonded to at least a portion of the hydrophilic polymeric unit. In a preferred embodiment, the bifunctional spacer is α-hydro-ω-hydroxypoly(oxy-1,2-ethanediyl)-bis-(1-hydroxbenzotriazolyl carbonate) (HPEOC). The coating can also include a reactive group, such as a primary or secondary amine, covalently bonded to the bifunctional spacer. In one embodiment, the hydrophilic polymeric unit and the bifunctional spacer are cross-linked with the plasma deposited double bond monomer.

The invention further includes a medical device for insertion into the body of a mammal, which medical device has at least one contacting surface for contacting bodily fluids or tissues, wherein the contacting surface has a coating of this invention. The contacting surface may include a metallic or polymeric material. The medical device may be a stent, catheter, shunt, valve, pacemaker, pulse generator, cardiac defibrillator, spinal stimulator, brain stimulator, sacral nerve stimulator, lead, inducer, sensor, seed, screw, anchor, anti-adhesion sheet, suture, needle, lens, joint or, in general, any implantable medical device known or hereafter developed.

The invention further includes a method for coating a surface with a hydrophilic and lubricious coating composition, the method including the steps of contacting a hydrophilic polymeric unit to the surface to be coated and cross-linking the hydrophilic polymeric unit by plasma deposition of a double bond monomer. The method may optionally include the additional steps of introducing a reactive group to the surface and contacting a bifunctional spacer with the reactive group under conditions whereby the bifunctional spacer is covalently bonded to the reactive group, it being understood that the hydrophilic polymeric unit is contacted to the surface to be coated with the bifunctional spacer under conditions whereby the hydrophilic polymeric unit is covalently bonded to the bifunctional spacer. The plasma employed is conventionally a radiofrequency plasma. In a preferred embodiment the plasma deposition is for at least five minutes, and preferably for at least ten minutes. The reactive group may be a primary amine or secondary amine, and if a secondary amine, may include plasma deposition of TMSAA. A primary object of the present invention is to provide a method to cross-link a polymeric unit coating by plasma deposition of a double bond monomer, such that a cross-linked lubricious coating results.

Another object of the present invention is to provide a coating that is both biocompatible and lubricious, including hydrophilic polymeric units cross-linked by means of a plasma deposited double bond monomer.

Another object of the present invention is to provide a coating with increased wear and resistance characteristics, resulting from plasma crosslinking utilizing a double bond monomer.

Another object of the present invention is to provide a coating wherein characteristics, including lubricity and wear resistance, may be altered by varying the plasma deposition time or plasma energy, or both, of the double bond monomer plasma.

Another object of the present invention is to provide a method for crosslinking a hydrophilic polymer that does not require pH adjustments, lengthy reaction times or chemical reaction solutions.

Another object of the present invention is to provide a coating including a bifunctional spacer covalently bonded to a reactive group anchored on a substrate surface, wherein the bifunctional spacers are cross-linked to hydrophilic polymeric units by means of plasma deposited double bond monomers.

Another object of the present invention is to provide a hydrophilic and lubricious cross-linked centeral that may be applied to any substrate, including metal, polymeric and ceramic substrates.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

Figure 1:
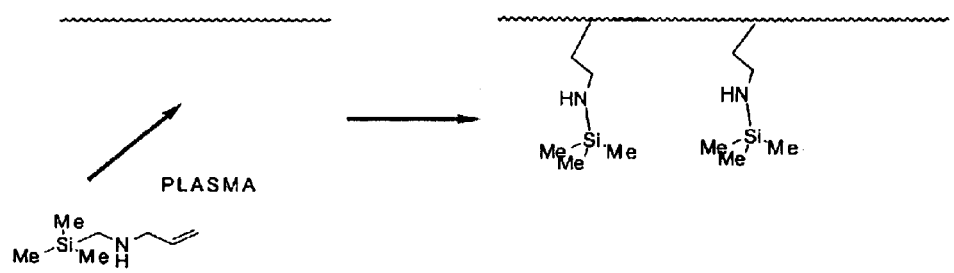
FIG. 1 depicts a chemical scheme for plasma deposition of amine reactive group, TMSM, on a substrate surface.

DESCRIPTION OF THE PREFERRED
EMBODIMENTS (BEST MODES FOR
CARRYING OUT THE INVENTION)

In a first aspect, the invention provides for cross-linking of hydrophilic polymeric units, such as an ethylene glycol derivative or complex carbohydrate, and preferably hydrophilic polymeric units containing either primary or secondary alcohol groups or both, by means of plasma deposition of a double bond monomer. The hydrophilic polymeric unit may be applied in solution, such as by means of a suitable solvent, by conventional means, including spraying, dipping, coating and the like. The double bond monomer preferably includes a C=C bond, but may also include monomers with C=N or C=O bonds. The double bond monomer is applied by means of plasma deposition, resulting in free radical formation and C—C bonds cross-linking the hydrophilic polymeric unit, such as through primary or secondary alcohol groups.

In a second aspect, the invention provides a lubricious and hydrophilic biocompatible coating with enhanced wear characteristics, which coating includes cross-linked hydrophilic polymeric units, such as an ethylene glycol derivative or complex carbohydrate that is cross-linked through a plasma deposition process utilizing a double bond monomer.

In a third aspect, the invention provides a coating wherein two or more co-polymers are cross-linked through a plasma deposition process utilizing a double bond monomer.

In a fourth aspect, the invention provides a coating including a first group introduced by any means, including plasma deposition, which first group provides a primary amine, secondary amine or other functional group, a second group that is a bifunctional spacer bound, preferably by a covalent bond, to the first group, and at least one third group that is a hydrophilic polymeric unit bound, preferably by a covalent bond, to the bifunctional spacer, wherein the at least one third group is cross-linked by means of plasma polymerization of a double bond monomer. The bifunctional spacer may constitute a co-polymer, such that the second group bifunctional spacer is cross-linked to the third group hydrophilic polymeric unit by means of plasma polymerization of the double bond monomer.

The process of the invention yields, in a comparatively simple and easily reproducible manner, smooth and continuous hydrophilic layers of polymerized hydrophilic polymeric units. The hydrophilic character of the surfaces, detectable from the smaller contact angle, is increased considerably, or provided in the first instance, by the process of the invention. The process can be carried out with a large number of different polymeric substrates and various hydrophilic polymeric units. The hydrophilic polymer layers are, in one embodiment, covalently bonded to the substrate, and cannot be detached from the substrate selectively with solvents and are therefore very durable. In another embodiment, the hydrophilic polymer layers are covalently bonded to a primer coating that is in turn attached to the substrate.

The following terms are defined as follows for the purposes of this disclosure:

A "plasma process" includes a capacitively coupled plasma deposition system. In one embodiment, a glow discharge is ignited between seven-inch square parallel plate electrodes made of aluminum. The distance between the two electrodes is 6.5 inches. The electrodes are both power driven at a radio frequency of 13.56 MHz, and the whole plasma chamber is grounded. The sample rack is made of Teflon and stainless steel set in the plasma glow zone and is electrically floating, and may be rotated during the plasma process to assure uniformity of plasma coating or surface modification on samples.

A "hydrophilic polymeric unit" includes polyethylene glycols (PEG), polyethylene oxides, and derivatives and related compounds thereof, such as activated PEG, derivatized PEG, and various other water-soluble and non-peptidic polymers, copolymers, terpolymers and mixtures thereof, and further includes glycosaminoglycans, including long chain linear polysaccharides such as heparin, hyaluronic acid, hyaluronan, cellulose, dextans, and methyl cellulose. Preferably the hydrophilic polymeric unit includes one or more primary or secondary alcohol groups, such as a hydroxyl group attached to a primary carbon or a hydroxyl group attached to a secondary carbon. Examples of hydrophilic polymeric units include PEG, polyalkylene glycol, polyoxyethylated polyol, polyolefinic alcohol, polyvinylpyrrolidone, polyvinyl alcohols, polyacrylamines, and the like, as well as glycosaminoglycans such as complex carbohydrates, including heparin, heparan sulfate, hyaluronic acid, hyaluronan, dextran, dextran sulfate, chondroitin sulfate, dermatan sulfate, dextrans, and the like, including but not limited to molecules including a mixture of variably sulfated polysaccharide chains composed of repeating units of d-glucosamine and either 1-iduronic or d-glucuronic acids, and derivatives of any of the foregoing. One preferred hydrophilic polymeric unit is 2,2'[(methylethylidine)-bis(4, 1-phenyleneoxymethylene)]-bis-oxirane-polymer (PEOC).

A "double bond monomer" includes any molecule that can be applied by means of plasma deposition and that contains a double bond, preferably a C=C bond, and less preferably a C=N or C=O bond. The C=C double bond can be present in most diverse functional groups, for example in alkenyl residues, such as vinyl or allyl residues, or in functional groups derived from unsaturated carboxylic acids or derivatives thereof, such as acrylic acid, methacrylic acid, the amides of these carboxylic acids or maleic acid. These compounds can also contain hydrophilic groups such as amine groups, acyloxy groups, carboxyl groups, carboxylic acid ester groups, carboxylic acid amide groups, carboalkoxy groups, nitrile groups, 1,2-epoxide groups, sulfuric acid esters and sulfonic acid, sulfinic acid, phosphoric acid, phosphonic acid and phosphinic acid groups, including their corresponding salts and esters, primary, secondary and tertiary amino groups, and acylamino groups, which can be incorporated as an open chain or in ring-polyalkylene oxide groups. The balance between hydrophilic and hydrophobic contents in the monomer determines the hydrophilicity of the monomer, and thus this factor may be utilized in determining a suitable monomer for a given purpose. Monomers that are suitable for use in this invention include gases, volatile liquids, or molecules that can be made to become volatile such that they can be introduced into a glow discharge plasma chamber. Examples of suitable monomers which may be utilized include propylene; ethylene; acrylic acid and derivatives thereof, such as for example acrylamide, N,N-dimethylacrylamide, acrylonitrile, methyl acrylate, 2-hydroxyethyl acrylate, 2-hydroxypropyl acrylate, 2-methoxyethyl acrylate, 2-ethoxyethyl acrylate, 4-hydroxybutyl acrylate and 1,4-butanediol diacrylate; methacrylic acid and corresponding derivatives thereof; carboxylic acid vinyl derivatives, such as for example vinyl acetate, N-vinylacetamide, N-vinylpyrrolidone-vinylsulfonic acids and alkali metal salts thereof, such as sodium vinylsulfonatealkenylarylsulfonic acids; styrene, styrene sulfonic acid and styrene sulfonate-vinyl ethers, such as vinyl methyl ether, vinyl ethyl ether, vinyl glycidyl ether, diethylene glycol divinyl ether and vinyl n-butyl ether; vinyl ketones, such as vinyl methyl ketone, vinyl ethyl ketone and vinyl n-propyl ketone; vinylamines, such as N-vinylpyrrolidine; polyalkylene compounds with terminal allyl, vinyl, acrylic or methacrylic groups, such as ethoxytetraethoxyethyl acrylate or methacrylate, allylamine, allyl alcohol, propylene, ethylene, and the like. It is contemplated that triple bond monomers are included within the definition of double bond monomers, so that triple bond monomers such as acetylene can also employed. A preferred double bond monomer is N-trimethylsilyl-allylamine of the formula $CH_2=CH-CH_2-NH-Si(CH_3)_3$ (TMSAA), which includes a C=C bond. Other preferred double bond monomers include ethylene ($CH_2=CH_2$), propylene ($CH_2=CH-CH_3$) and allyl alcohol ($CH_2=CH-CH_2-OH$). The double bond monomer can constitute a hydrophilic polymeric unit as defined above, provided it contains at least one double bond.

A "bifunctional spacer" is a molecule that can be bound by any means to two different molecules, such as a functional group on a substrate and a hydrophilic polymeric unit. A bifunctional spacer preferably forms covalent bonds with amine groups, and further preferably constitutes a hydrophilic polymeric unit. The bifunctional spacer can be any of a number of bifunctional agents that react with amines, such as bis-variants of PEG, polyethylene oxide, and related PEG compounds wherein the functional groups are composed of homo- or hetero-functional groups, with representative functional groups including succinimymidyl esters, nitrophenyl activated esters, azidophenyl groups, maleimido groups, imido esters, carbodiimides, benzotriazole carbonates, or aldehdye groups. A preferred bifunctional spacer is α-hydro-ω-hydroxypoly(oxy-1,2-ethanediyl)-bis-(1-hydroxbenzotriazolyl carbonate) (HPEOC), which contains benzotriazole carbonate functional groups.

A "substrate" is any surface to be coated by the method of this invention, or with the coating of this invention. Substrates thus include homo- and co-polymers, for example polyolefins, such as polyethylene, polypropylene, polyisobutylene, polybutadiene, polyisoprene; naturally occurring rubbers and polyethylene-copropylene; halogen-containing polymers, such as polyvinyl chloride, polyvinylidene chloride, polychloroprene, polytetrafluorothylene and polyvinylidene fluoride; polymers and co-polymers of vinylaromatic monomers, such as polystyrene, polyvinyloluene, polystyrene-co-vinyltoluene, polystyrene-co-acrylonitrile and polystyrene-co-butadiene-co-acrylonitrile; polycondensates, such as polyesters like polyethylene terephthalate and polybutylene terephthalate; polyamides, such as polycaprolactam, polylaurolactam and the polycondensate of adipic acid and hexamethylenediamine; polyether-block amides, such as laurolactam and polyethylene glycol with on average 8-, 12- or 16-ethyleneoxy groups; poly caprolactone; poly lactide; polyglycolide, and generally polyurethanes, polyethers, polycarbonates, polysulfones, polyether ketones, polyesteramides and -imides, polyacrylonitrile and polyacrylates and polymethacrylates. Blends of two or more polymers or co-polymers can also be coated by the method of this invention, as can combinations of various plastics that are joined to one another by adhesive bonding, welding or fusion, including the transition regions. A substrate also includes metals, such as stainless steel, nitinol, titanium, and blends or composites thereof, and ceramics.

The substrate may form a surface structural component of a medical device intended to contact blood or other tissues, such as stents, needles, sutures, catheters, shunts, grafts, and other medical devices known in the art. The surface structural component may include a plate, curved surfaces, mesh, coil, wire, inflatable balloon, or any other device or structure which is capable of being implanted at a target location, including intravascular target locations, intralumenal target locations, target locations within solid tissue, such as for the treatment of tumors, and the like. The device can be intended for permanent or temporary implantation. Such devices may be delivered by or incorporated into intravascular and other medical catheters.

The methods and coatings of the invention find primary application in medical devices, and particularly blood- or tissue-contacting medical devices wherein lubricity is desired, such as grafts, catheters, guidewires, sutures, needles, stents and the like. The coating provides a surface with good handling characteristics when dry, but which becomes lubricious upon contact with an aqueous solution, such as a bodily fluid. However, the methods and coatings of the invention can be used with other medical devices wherein lubricity is desired, including contact lenses, bandages and other wound covers, and the like, as well as in pharmaceutical, cosmetic and other applications where lubricity, particularly coupled with biocompatibility, is desired on one or more surfaces.

In one embodiment, secondary amine groups are introduced onto the surface of a substrate by plasma deposition of a secondary amine-containing substance, such as TMSAA, as is shown in the scheme of FIG. 1. In FIG. 1, TMSAA is shown attached to a substrate by means of a plasma, resulting in a secondary amine with a terminal —$Si(CH_3)_3$ group that can be cleaved by means of an aqueous media. For example, polyethylene and similar polymeric substrates can be so treated with TMSAA to introduce reactive amines. TMSAA is integrated by plasma grafting using operational parameters sufficient to introduce the requisite density of secondary amine groups without adverse surface modification. Plasma grafting may proceed at, for example, operational parameters of 8 minutes deposition time at 65 mTorr, 45 W and a flow rate of TMSAA of 42 standard cubic centimeters per minute (sccm). Alternative methods of introducing primary or secondary amines can also be utilized, including plasma processes to introduce primary amine groups into a surface using ammonia gas in a plasma chamber, as described in U.S. Pat. No. 5,338,770, and various chemical modification methods, as described in U.S. Pat. No. 6,265,016, entitled *Process for the Preparation of Slippery, Tenaciously Adhering, Hydrophilic Polyurethane Hydrogel Coatings, Coated Polymer and Metal Substrate Materials, and Coated Medical Devices*, such as use of aminosilanes.

For certain applications, such as metal-containing substrates, glow-discharge plasma treatment with a siloxane derivative, such as 1,3,5,7-tetramethylhydrocyclotetrasiloxane (TMCTS), followed by integration by plasma grafting of an amine-rich reagent, such as TMSAA, is preferred. The plasma process with TMCTS creates a "primer" coating of polymeric TMCTS. In this embodiment, any hydrocyclsiloxane monomer may be employed, including 1,3,5,7-tetramethylhydrocyclotetrasiloxane, 1,3,5,7,9-pentamethylhydrocyclopentasiloxane, 1,3,5,7,9,11-hexamethylhydrocyclohexasiloxane, or a mixture of 1,3,5,7,9-pentamethylcyclopentasiloxane and 1,3,5,7,9,11-hexamethylcyclohexasiloxane monomers, as taught in U.S. Pat. No. 5,463,010, incorporated herein by reference. In a related embodiment, the surface, with metal or polymeric surfaces, may be initially modified using nitrogen- and oxygen-containing plasma as taught in International Patent Application PCT/US00/34945, *Plasma-Deposited Coatings, Devices and Methods*, incorporated herein by reference.

Following introduction of a primary or secondary amine to the surface of the substrate, the substrate may be washed with a suitable organic solvent prior to proceeding with further reactions. Depending on the substrate and the primary or secondary amine group introduced, suitable organic solvents include methylene chloride, acetonitrile and the like.

Figure 2:
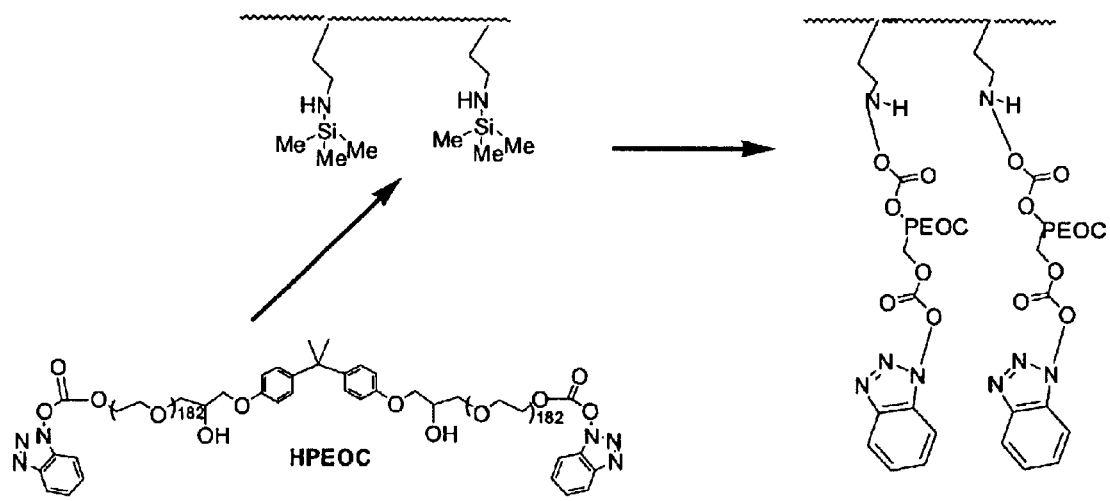
FIG. 2 depicts a chemical scheme for reaction of HPEOC with TMSAA.

A bifunctional spacer may then be attached to the primary or secondary amine, as is shown generally in the scheme of FIG. 2, depicting addition of HPEOC and cleaving of the —$Si(CH_3)_3$ group, resulting in PEOC conjugated by means of a covalent bond to the introduced secondary amine, the PEOC sequence further including a terminal benzotriazole carbonate group at the distal end. A preferred bifunctional spacer is HPEOC, which can be applied by immersing the surface in a solution including HPEOC. In one embodiment, 5% HPEOC in acetonitrile is employed; in another embodiment 5% HPEOC in methylene chloride is employed. The HPEOC reacts with the secondary amine on the surface resulting in conjugation, such that one functional group on the HPEOC is utilized for the covalent bond with the secondary amine. HPEOC is typically supplied in methylene chloride and is utilized in a large molar excess, such that the conjugated agent consumes only one functional group. Unreacted bifunctional spacer may be removed, such as by rinsing in a suitable solvent.

Figure 3:
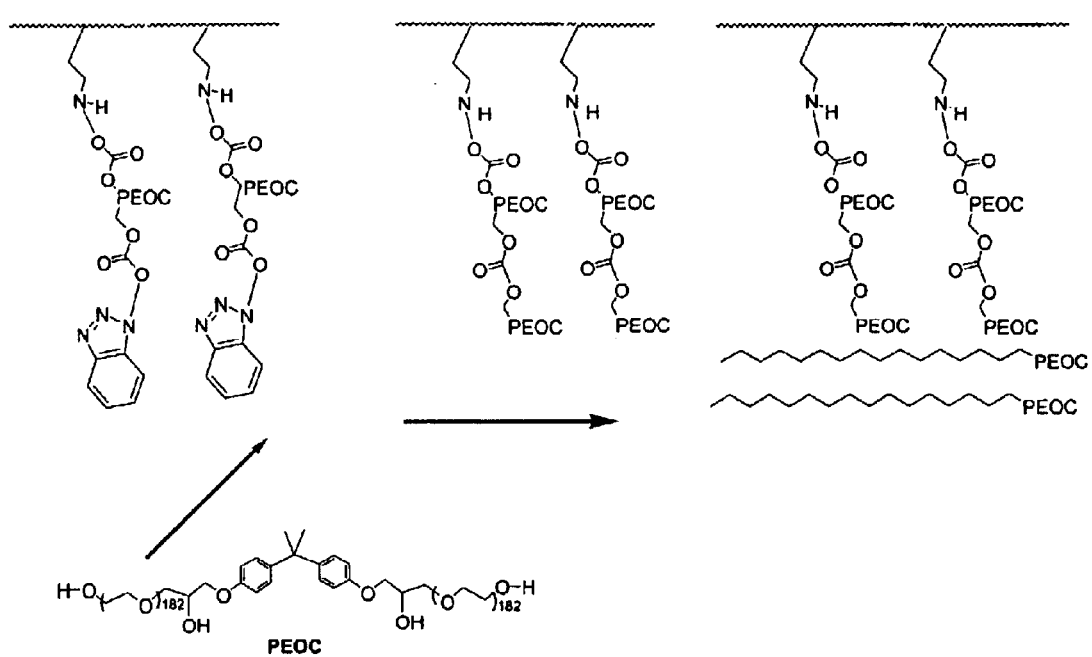
FIG. 3 depicts a chemical scheme for reaction of PEOC with HPEOC.

A hydrophilic polymeric unit is then added, such as by dipping or immersing the bifunctional spacer complexed surface in a solution including the hydrophilic polymeric unit. Where PEOC is employed as the hydrophilic polymeric unit, a 10% solution may be employed. The monomers can be used individually or as a mixture adapted to the particular intended use. A coating of a homo- or co-polymer is obtained accordingly on the substrate. The monomers are in general employed as 1% to 40%, advantageously as 5% to 20%, strength by weight solutions. A conventional solvent that can be employed is methylene chloride. The scheme of FIG. 3 illustrates the reaction of the hydrophilic polymeric unit PEOC with the remaining functional group of the surface-bound bifunctional spacer HPEOC, resulting in both covalently complexed repeating PEOC units and PEOC associated therewith but not covalently complexed thereto. The hydrophilic polymeric unit is preferably applied at a concentration such that a thin film of unreacted hydrophilic polymeric unit is left as an overcoating. The thin film is dried onto the surface.

Figure 4:
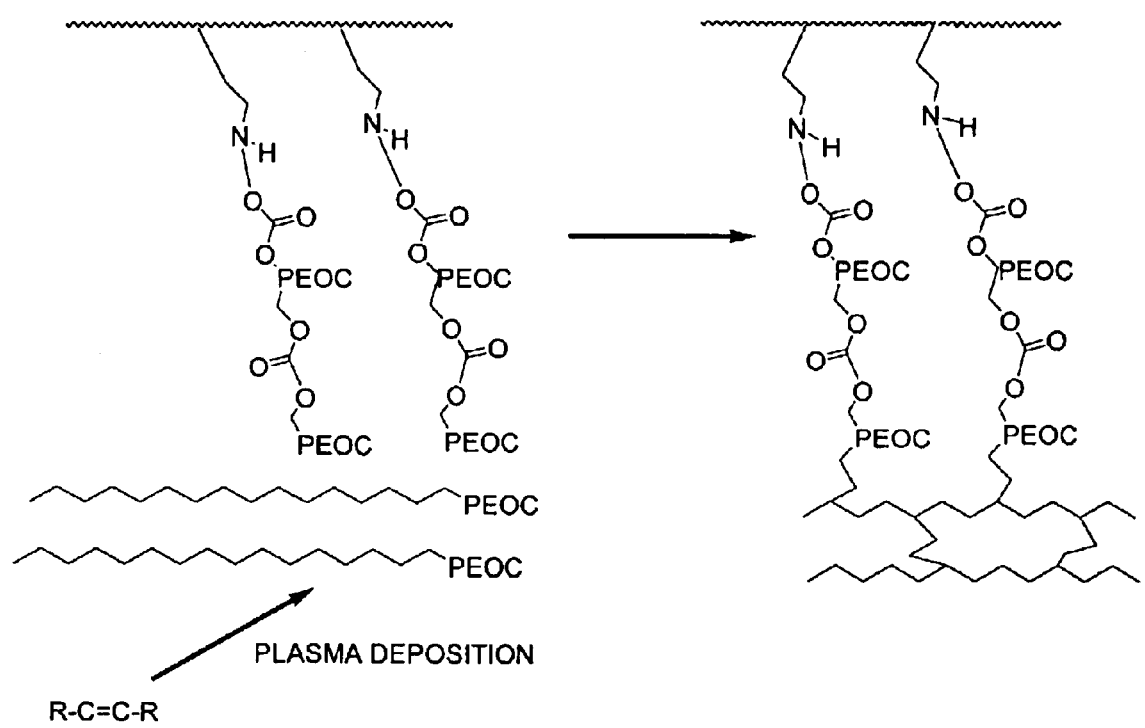
FIG. 4 depicts a chemical scheme for crosslinking PEOC with a plasma deposited double bond monomer.

As is shown in the scheme of FIG. 4, a double bond monomer, depicted as R—C=C—R, is reacted with the hydrophilic polymeric unit by means of a plasma, resulting in crosslinking of the hydrophilic polymeric unit in the thin film, including crosslinking with hydrophilic polymeric units bound to the bifunctional spacer and the underlying bifunctional spacer, if provided. While FIG. 4 illustrates crosslinking between adjacent PEOC units not covalently complexed and between covalently complexed PEOC and uncomplexed PEOC, it is to be understood that the reaction as depicted in FIG. 4 can further include crosslinking between any of the foregoing and the bifunctional spacer, such as the PEOC resulting from complexation of the HPEOC bifunctional spacer. It is hypothesized, without wishing to be bound by theory, that crosslinking is primarily through primary or secondary alcohols, or both, in the hydrophilic polymeric unit, effected by free radicals formed by the double bond monomer plasma. Thus, for example, if PEOC is the hydrophilic polymeric unit and HPEOC is the bifunctional spacer, it may readily be seen that crosslinking is possible between parallel PEOC chains, between covalently complexed PEOC and free PEOC, such as through an alcohol or through activation and displacement of a benzotriazole group, and between either complexed PEOC or free PEOC and HPEOC, again through similar groups.

TMSAA is a preferred double bond monomer because the compound can also be used to introduce secondary amine groups, and because the trimethylsilyl group functions as a protecting group, in that it is spontaneously cleaved in an aqueous environment, but is stable in plasma processes, and thus prevents inadvertent crosslinking between amines.

It has been discovered that, in general, a longer plasma process at lower energy results in more crosslinking, and apparently improved lubricity, than a shorter plasma process at higher energy. Thus, for example, in one embodiment TMSAA plasma for 10 minutes at 45 W, 65 mTorr and 42 sccm is employed. The plasma process parameters may be modified to produce the desired effect using the methods and examples described herein.

While for many applications introduction of a reactive amine or other group and attachment of a bifunctional spacer provides advantageous results, for other applications it may only be necessary to apply the hydrophilic polymeric unit and subsequently cross-link in situ the polymeric units by means of a double bond monomer plasma. That is, the invention includes films, coatings and other compositions wherein a hydrophilic polymeric unit is applied without utilizing a bifunctional spacer or introducing a reactive group.

The invention is further illustrated by the following non-limiting examples.

EXAMPLE 1

TMSAA Plasma Grafting and HPEOC Reaction

Strips of polyethylene were used as the substrate. TMSAA was integrated onto the plastic by plasma grafting with operational parameters of 8 minutes deposition time at 65 mTorr, 45 W, and a flow rate of 42 sccm. The TMSAA plasma grafted strips were rinsed for 5 minutes in methylene chloride, and then immersed in a solution of 5% HPEOC in methylene chloride for 20 minutes. Unreacted HPEOC was removed in a 5 minute rinse in methylene chloride.

EXAMPLE 2

Stainless Steel Modification

Stainless steel wafers (0.75 cm×0.75 cm) were treated in a glow-discharge plasma with a mixture of $NH_3/O_2$ for 45 seconds. The plasma was generated at 110 W and pressure of 50 mTorr using a total mass flow rate of 50 sccm. The materials were then treated by glow-discharge plasma with the siloxane derivative TMCTS for 4 seconds, causing the TMCTS to polymerize and attach to the substrate. The TMCTS plasma was generated at 83 W, 55 mTorr, and a flow rate of 84 sccm. TMSAA was then integrated into the film by plasma grafting with operational parameters of 4 minutes of deposition time, 65 mTorr, 35 W, and a flow rate of 42 sccm. The resulting coated steel wafers were rinsed for 5 minutes in methylene chloride. The wafers were immersed in a solution of 5% HPEOC in methylene chloride for 20 minutes. Unreacted HPEOC was removed in a 5 minute rinse in methylene chloride.

EXAMPLE 3

TMSAA Crosslinking of PEOC/HPEOC

Strips of polyethylene were used as the substrate. TMSAA was integrated onto the plastic by plasma grafting with operational parameters of 8 minutes of deposition time, 65 mTorr, 45 W, and a flow rate of 42 sccm. The TMSAA plasma-grafted polyethylene strips were then rinsed for 5 minutes in methylene chloride, followed by immersion in a solution of 5% HPEOC in methylene chloride for 20 minutes. Unreacted HPEOC was removed in a 5 minute rinse in methylene chloride. The HPEOC reacted polyethylene strips were then immersed in a 10% solution of PEOC for 20 minutes and air-dried. The PEOC and HPEOC were then cross-linked in a plasma process using plasma crosslinking with TMSAA as the crosslinking agent. The TMSAA cross-linked plasma had operational parameters of 16 minutes of deposition time, 65 mTorr, 45 W, and a flow rate of 42 sccm. The materials were then immersed in methylene chloride for 5 minutes and air-dried.

EXAMPLE 4

TMSAA Crosslinking of Hyaluronic Acid

Strips of polyethylene were used as the substrate. TMSAA was integrated onto the plastic by plasma grafting with operational parameters of 4 minutes of deposition time, 65 mTorr, 45 W, and a flow rate of 42 sccm. The TMSAAS plasma-grafted polyethylene strips were then rinsed for 5 minutes in methylene chloride, followed by immersion in a solution of 5% HPEOC in methylene chloride for 20 minutes. Unreacted HPEOC was removed in a 5 minute rinse in methylene chloride. The HPEOC reacted polyethylene strips were then immersed in a 0.5% solution of hyaluronic acid for 20 minutes and air-dried. The resulting product was cross-linked in a plasma process using plasma crosslinking with TMSAA as the crosslinking agent. TMSAA plasma had operational parameters of 16 minutes of deposition time, 65 mTorr, 45 W, and a flow rate of 42 sccm. The materials were then immersed in methylene chloride for 5 minutes and air-dried.

EXAMPLE 5

Guide Wire TMSAA Crosslinking of PEOC/HPEOC

Guide wires were treated in a glow-discharge plasma with a mixture of $NH_3/O_2$ for 45 seconds. The plasma was generated at 110 W under a vacuum of 50 mTorr and using a total mass flow rate of 50 sccm. The materials were then treated by glow-discharge plasma with the siloxane derivative TMCTS for 4 seconds, resulting in TMCTS polymeri attached to the substrate. The TMCTS plasma was generated at 83 W, 55 mTorr, and flow rate of 84 sccm. TMSAA was then integrated into the film by plasma grafting using operational parameters of 4 minutes of deposition time, 65 mTorr, 35 W, and a flow rate of 42 sccm. The coated wires were then rinsed for 5 minutes in acetonitrile, followed by immersion in a solution of 5% HPEOC in acetonitrile for 20 minutes. Unreacted HPEOC was removed in a 5-minute rinse in acetonitrile. The coated wires were then immersed in a 10% solution of PEOC for 20 minutes and air-dried. The surface of the coated wires was cross-linked in a plasma process using TMSAA as the crosslinking agent. The TMSM plasma had operational parameters of 12 minutes of deposition time, 65 mTorr, 45 W, and a flow rate of 42 sccm. The materials were then immersed in acetonitrile for 5 minutes and air dried.

EXAMPLE 6

Double Bond Monomers

To evaluate the critical effect of monomers containing at least one double bond on plasma crosslinking of PEOC, three different monomers were used on HPEOC/PEOC coated stainless steel substrates: ethylene ($CH_2=CH_2$), ethane ($CH_3—CH_3$), and allyl alcohol ($CH_2=CH—CH_2—OH$). Stainless steel strips (1"x3") were used as the substrate. Strips were first overlayered with a siloxane polymer y plasma treatment in glow-discharge plasma of $NH_3O_2$ followed by treatment in a plasma of TMCTS. The $NH_3/O_2$ plasma was generated for 45 seconds at 110 W at a pressure of 50 mTorr and a total mass flow rate of 50 sccm; the TMCTS plasma for 4 seconds at 83 W, 55 mTorr, with a flow rate of 84 sccm. TMSAA was integrated into the substrate for 4 minutes using operational parameters of 65 mTorr, 35 W, and a mass flow rate of 42 sccm. The plasma-coated stainless steel strips were rinsed for 5 minutes in methylene chloride, dip-coated in a solution of 5% HPEOC in methylene chloride for 20 minutes, and rinsed for 5 minutes in methylene chloride to remove unreacted HPEOC. After the final rinse, the HPEOC reacted stainless steel strips were dip-coated in a 10% solution of PEOC in methylene chloride for 20 minutes and dried in air.

The coated steel strips were exposed to a plasma formed with one of ethylene, ethane, or allyl alcohol. Three different plasma parameters were used for each different monomer: (1) 45 W, 6 minutes, 65 mTorr and 42 sccm; (2) 45 W, 10 minutes, 65 mTorr and 42 sccm; and (3) 90 W, 6 minutes, 65 mTorr and 42 sccm. After plasma process, the resulting coated steel strips were rinsed in running de-ionized water for 20 minutes and air dried.

A comparison of surface lubricity was made and the results indicated that plasmas of ethylene and allyl alcohol produced crosslinking on the PEOC surface and substantially improved lubricity. The most favorable condition for high crosslinking was at a lower power and longer time, that is, 45 W for 10 minutes, at 65 mTorr and a flow rate of 42 sccm. The ethane plasma did not provide any improvement on surface lubricity, and actually decreased lubricity compared to coated strips without the last plasma step. In a separate test, propylene ($CH_2=CH—CH_3$) yielded results comparable to ethylene or TMSAA.

EXAMPLE 7

Pull Force Testing

Pull force testing was performed on polyethylene strips with and without the coating as in Example 3. The pull force was measured with a tensile strength monitor (Instron). The pulling force was determined as the average load in pounds needed to displace the strip from an initial setting of 0.3" to a final position of 1.1" under wet conditions. Polyethylene samples with no coating (controls) required an average force of 6.413 lbs to affect displacement. Polyethylene samples treated with the TMSAA cross-linked PEOC coating as in Example 3 required an average force of 0.671 lbs.

EXAMPLE 8

Reduction of Pulling Force by Increasing TMSAA Plasma Treatment Time

Polyethylene specimens were processed as in Example 3 except that the time of the final TMSAA plasma was varied in 4-minute intervals from 4 minutes to 16 minutes. The specimens were then subjected to pull-force testing as in Example 7. The data was then converted to percentages. Increasing the time of the TMSAA crosslinking plasma decreased the force need to affect displacement. Plasma times of 4-, 8-, 12-, and 16 minutes resulted in a decrease in force relative to uncoated specimens of 75.0%, 83.7%, 84.8%, and 87.0%, respectively.

EXAMPLE 9

Effect of Varying Wattage of TMSAA Plasma Treatment

Stainless steel specimens were processed as in Example 5 except that the wattage used in the final TMSAA crosslinking plasma treatment was either 35 W or 45 W. The specimens were tested by pull force testing as in Example 7. With no treatment, the mean pulling force was 5.637 lb/f. Using the coating procedure and 45 W in the final TMSAA crosslinking step, the mean pulling force was reduced by 91.2% to 0.497 lbs. Using the coating procedure and 35 W in the final TMSAA crosslinking step, the mean pulling force was reduced by 89.1% to 0.613 lbs.

EXAMPLE 10

Durability of Coating

Polyethylene specimens were processed as in Example 3. The specimens were tested by pull force testing as in Example 7. The force measurements were serially repeated for 5 pulls and the average pull load is presented in Table 1; the data indicates that the coating is durable over the testing cycle.

TABLE 1

HPEOC AS THE HYDROPHILIC POLYMERIC UNIT

| PULL NUMBER | AVERAGE PULL LOAD IN lb/f |
|---|---|
| 1 | 0.671 |
| 2 | 0.850 |
| 3 | 0.840 |
| 4 | 0.803 |
| 5 | 0.807 |

Polyethylene specimens were processed as in Example 4. The specimens were tested by pull force testing as in Example 7. The force measurements were serially repeated for 5 pulls and the average pull load is presented in Table 2; the data indicates that the coating is durable over the testing cycle.

TABLE 2

HYALURONIC ACID AS THE HYDROPHILIC POLYMERIC UNIT

| PULL NUMBER | AVERAGE PULL LOAD IN lb/f |
|---|---|
| 1 | 0.298 |
| 2 | 0.298 |
| 3 | 0.332 |
| 4 | 0.340 |
| 5 | 0.324 |

EXAMPLE 11

Surface Lubricity Testing 310 stainless steel straps (1"×3") were used, with initially cleaning using Acationox™ detergent and rinsing. Strips were divided into groups, with treatment as shown below. A surface lubricity test was performed using an Imada, Inc. DPS-0.5 digital force gauge with measurement controlled with Imada SW-1 data acquisition software. The digital force gauge was mounted on a stepping motor driven system, such that the digital force gauge could be moved at a constant speed. A metal flat head weighing 22 g with a rubber layer was used as the load pad, with samples placed in a container filled with distilled water and the load pad placed on the sample surface. Pulling force was measured by pulling the load pad; the lower the pulling force, the better lubricity. Results are shown in Table 3.

TABLE 3

| Coating Conditions | Pulling force Newton Mean | Std Dev | Number of pulls | Number samples tested |
|---|---|---|---|---|
| Plasma Coating/HPEOC/PEOC | 0.0281 | 0.0126 | 3 | 23 |
| Plasma Coating/HPEOC/PEOC/ TMSAA | 0.0219 | 0.0024 | 3 | 10 |
| HPEOC/PEOC | 0.0743 | 0.0046 | 30 | 3 |
| HPEOC/PEOC/TMSAA | 0.0214 | 0.0021 | 30 | 3 |
| HPEOC/TMSAA | 0.0246 | 0.0016 | 30 | 3 |
| PEOC/TMSAA | 0.0393 | 0.0062 | 30 | 3 |
| HPEOC only | 0.0261 | 0.0037 | 30 | 3 |
| TMSAA only | 0.2038 | 0.0218 | 30 | 3 |
| SS Control (Clean Sample) | 0.157 | 0.034 | 3 | 7 |

In Table 3, "Plasma Coating" consists of three steps: $NH_3/O_2$ etching for 45 seconds, TMCTS plasma coating for 4 seconds and TMSAA plasma grafting, all as in Example 2; "HPEOC" consists of dip coating in 5% HPEOC in methylene chloride for 20 minutes as in Example 2; "PEOC" consists of dip coating in 10% PEOC in methylene chloride for 20 minutes as in Example 6; and "TMSAA" consists of a cross-linking process at 45 W, 65 mTorr, 42 sccm for 10 minutes as in Example 6. The best results were obtained with HPEOC/PEOC/TMSAA (0.0214±0.0021) and Plasma Coating/HPEOC/PEOC/TMSAA (0.0219±0.0024); however, HPEOC/TMSAA yielded good results (0.0246±0.0016). While Plasma Coating/HPEOC/PEOC yielded mean values approximating the foregoing, the standard deviation in the absence of crosslinking was unacceptably high.

EXAMPLE 12

Surface Durability Test

Stainless steel strips as in Example 11 were prepared and subjected to durability testing. The results are shown in Table 4.

TABLE 4

| Coating Conditions | Pulling force of 2nd pull Mean | Std Dev | Pulling force of 30th pull Mean | Std Dev | % Increase from 2nd to 30th pull |
|---|---|---|---|---|---|
| Plasma Coating/ HPEOC/PEOC | 0.0353 | 0.0037 | 0.0515 | 0.0107 | 46% |
| Plasma Coating/ HPEOC/PEOC/ TMSAA | 0.0237 | 0.0048 | 0.0281 | 0.0016 | 19% |
| HPEOC/PEOC | 0.0596 | 0.0039 | 0.079 | 0.0058 | 33% |
| HPEOC/PEOC/ TMSAA | 0.0177 | 0.0005 | 0.0215 | 0.0018 | 21% |
| HPEOC/TMSAA | 0.0218 | 0.0039 | 0.0232 | 0.0012 | 6% |
| PEOC/TMSAA | 0.0255 | 0.0013 | 0.0414 | 0.0078 | 62% |
| HPEOC only | 0.0209 | 0.0017 | 0.0303 | 0.0035 | 45% |
| TMSAA only | 0.2168 | 0.0068 | 0.1951 | 0.0132 | -10% |

"Coating Conditions" have the meanings given in Example 11.

EXAMPLE 13

Surface Lubricity of Stainless Steel Wire

Stainless steel wire samples, 5" long by 0.015" diameter, were prepared as in Example 11. The results obtained using the methods of Example 11 are shown in Table 5.

TABLE 5

| Coating Conditions | Tests | Pulling force (Newton) | Mean | Standard Deviation | % Decrease (v. Control) |
|---|---|---|---|---|---|
| Clean wire (Control) | 1 | 0.2252 | 0.2377 | 0.0211 | 0% |
| | 2 | 0.2621 | | | |
| | 3 | 0.2259 | | | |
| Plasma Coating/ HPEOC/PEOC | 1 | 0.1972 | 0.1890 | 0.0147 | 20% |
| | 2 | 0.1977 | | | |
| | 3 | 0.1720 | | | |
| Plasma Coating/ HPEOC/PEOC/ TMSAA | 1 | 0.0338 | 0.0288 | 0.0044 | 88% |
| | 2 | 0.0261 | | | |
| | 3 | 0.0264 | | | |

"Coating Conditions" have the meanings given in Example 11.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A plasma cross-linked hydrophilic and lubricious coating comprising a hydrophilic polymeric unit cross-linked in situ with a plasma deposited double bond monomer.

2. The coating of claim 1 wherein the hydrophilic polymeric unit comprises an ethylene oxide with one or more primary or secondary alcohol groups.

3. The coating of claim 2 wherein the hydrophilic polymeric unit comprises 2,2'[(methylethylidine)-bis(4,1-phenyleneoxymethylene)]-bis-oxirane-polymer (PEOC).

4. The coating of claim 1 wherein the hydrophilic polymeric unit comprises a glycosaminoglycan.

5. The coating of claim 4 wherein the hydrophilic polymeric unit comprises a long chain linear polysaccharide selected from the group consisting of heparin, hyaluronic acid, hyaluronan, dextran, cellulose and methyl cellulose.

6. The coating of claim 1 wherein the double bond monomer comprises a C=C, C=N or C=O double bond.

7. The coating of claim 6 wherein the double bond monomer comprises a member selected from the group consisting of N-trimethylsilyl-allylamine (TMSAA), ethylene, propylene and allyl alcohol.

* * * * *